US006492180B2

(12) United States Patent
Brown et al.

(10) Patent No.: US 6,492,180 B2
(45) Date of Patent: *Dec. 10, 2002

(54) NON-INVASIVE TRANSDERMAL DETECTION OF ANALYTES

(75) Inventors: Larry R. Brown, Newton, MA (US); Elazer Edelman, Brookline, MA (US); David Tseng, Burlington, MA (US)

(73) Assignee: Transderm Technologies LLC, San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/339,147

(22) Filed: Jun. 24, 1999

(65) Prior Publication Data

US 2002/0019055 A1 Feb. 14, 2002

Related U.S. Application Data

(60) Provisional application No. 60/090,459, filed on Jun. 24, 1998.

(51) Int. Cl.$^7$ .................. G01N 33/20; C07D 207/26; A61K 9/70
(52) U.S. Cl. ................. 436/77; 436/76; 548/543; 424/449
(58) Field of Search .............. 548/543; 436/73, 436/169, 74, 77, 76; 424/449; 524/910; 600/362, 584; 435/7.1, 287.2, 287.8; 530/388.85, 389.8, 391.1

(56) References Cited

U.S. PATENT DOCUMENTS

| | | | |
|---|---|---|---|
| 4,039,664 A | 8/1977 | Stoughton et al. .......... 424/180 |
| 4,321,252 A | * 3/1982 | Keith et al. .................... 424/28 |
| 4,537,776 A | 8/1985 | Cooper ........................ 514/424 |
| 4,706,676 A | 11/1987 | Peck |
| 4,767,402 A | 8/1988 | Kost et al. ..................... 604/22 |
| 4,780,212 A | 10/1988 | Kost et al. .................. 210/646 |
| 4,819,645 A | 4/1989 | Peck |
| 4,821,733 A | 4/1989 | Peck |
| 4,909,256 A | 3/1990 | Peck |
| 4,921,757 A | 5/1990 | Wheatley et al. ......... 428/402.2 |
| 4,948,587 A | 8/1990 | Kost et al. .................. 424/435 |
| 4,956,301 A | * 9/1990 | Ismail et al. .................. 436/87 |
| 4,960,467 A | 10/1990 | Peck |
| 5,203,327 A | 4/1993 | Schoendorfer et al. |
| 5,262,165 A | * 11/1993 | Govil et al. ................. 424/448 |
| 5,422,361 A | 6/1995 | Munayyer et al. .......... 514/408 |
| 5,458,140 A | 10/1995 | Eppstein et al. ............. 128/632 |
| 5,527,832 A | * 6/1996 | Chi et al. .................. 514/772.4 |
| 5,532,136 A | * 7/1996 | Carlson et al. ............. 435/7.92 |
| 5,547,467 A | 8/1996 | Pliquett et al. ............... 604/20 |
| 5,589,346 A | 12/1996 | Kanan et al. |
| 5,667,491 A | 9/1997 | Pliquett et al. ............... 604/50 |
| 5,756,117 A | 5/1998 | D'Angelo et al. .......... 424/449 |
| 5,814,599 A | 9/1998 | Mitragotri et al. ............. 514/3 |
| 5,883,115 A | 3/1999 | Santus et al. ................ 514/413 |
| 5,899,856 A | 5/1999 | Schoendorfer et al. ..... 600/362 |
| 5,911,223 A | 6/1999 | Weaver et al. .............. 128/898 |
| 5,947,921 A | 9/1999 | Johnson et al. ............... 604/22 |
| 6,002,961 A | 12/1999 | Mitragotri et al. ............ 604/20 |
| 6,018,678 A | 1/2000 | Mitragotri et al. ............ 604/20 |
| 6,041,253 A | 3/2000 | Kost et al. ..................... 604/20 |
| 6,173,202 B1 | 1/2001 | Eppstein ....................... 604/20 |
| 6,183,434 B1 | 2/2001 | Eppstein ....................... 604/22 |
| 6,190,315 B1 | 2/2001 | Kost et al. .................. 600/309 |
| 6,251,083 B1 | 6/2001 | Yum et al. ................... 600/584 |

FOREIGN PATENT DOCUMENTS

| | | |
|---|---|---|
| FR | 2 612 521 | 9/1988 |
| WO | WO 92/21772 A1 | 12/1992 |
| WO | WO 98/00194 | 1/1998 |
| WO | WO 99/13336 | 3/1999 |
| WO | WO 99/23479 | 5/1999 |
| WO | WO 99/34857 | 7/1999 |
| WO | WO 00/29466 | 5/2000 |
| WO | WO 00/35351 | 6/2000 |
| WO | WO 00/35357 | 6/2000 |
| WO | WO 00/57177 | 9/2000 |

OTHER PUBLICATIONS

Sugibayashi et al., "Effect of Several Penetration Enhancers on the Percutaneous Absorption of Indomethacin in Hairless Rats", Chem. Pharm. Bull (1998) vol. 36 No. 4 pp. 1519–1528.*

(List continued on next page.)

Primary Examiner—John S. Brusca
Assistant Examiner—Marjorie A. Moran
(74) Attorney, Agent, or Firm—Fish & Neave; Nicola A. Pisano; Daniel M. Becker (57) ABSTRACT

A method and apparatus for non-invasive extraction and/or detection of chemicals such as heavy metals, drugs such as cocaine and analytes such as blood glucose has been developed. A patch or hydrogel containing a reagent such as N-methyl pyrrole, or a similar compound, is used to extract the chemical or analyte to be measured through the skin or hair. This method is most useful for detecting analytes which are generally present in relatively constant blood concentrations. The method is particularly useful for the detection of heavy metals such as lead, lithium, copper, iron, and has been demonstrated to be useful with drugs such as cocaine and acetominaphen, and metabolic analytes like blood glucose. In the preferred embodiment, the method involves the use of the water miscible solvent N-methyl pyrrolidone (NMP) in an aqueous solution which is incorporated into an adsorbent pad or hydrogel. This adsorbent pad is placed on the skin for a defined time period, removed and then analyzed for the substance of interest. An analytical method can also be incorporated as part of the adsorbent pad in order to conduct both the extraction of the chemical of interest and the assay in situ. Examples demonstrating the very broad range of materials which can be extracted. Comparative examples demonstrate that the same results cannot be obtained using other reagents such as dimethylsulfoxide (DMSO).

29 Claims, 10 Drawing Sheets

OTHER PUBLICATIONS

Bescos et al., "Laser–induced breakdown spectroscopy of Al–samples: application to chemical analysis of metallic elements," *Laser Chem.* 16(2):75–82 (1995).

Jaffe, "Toxic mineral detection by provocation: a noninvasive test for bioaccumulation of possibly toxic divalent cations including lead, mercury arsenic, cadmium, nickel and aluminum, a proposal," *International Clinical Nutrition Rev.* 10(2):340–342 (1990).

Kalef–Ezra et al., "Radiation risk to the human conceptus from measurement of material tibial bone lead by L–line X–ray fluorescence," *Health Physics* 58 (2):217–218 (1990).

Kosnett et al., "Factors influencing bone lead concentration in a suburban community assessed by noninvasive x–ray fluorescence," *JAMA* 271(3):197–203 (1994).

Kost et al., "Transdermal monitoring of glucose and other analytes using ultrasound", *Nature Medicine*, vol. 6, No. 3 (2000) pp. 347–350.

Lyubchenko, "Noninvasive methods for diagnosis of occupational diseases," Klinicheskaya Laboratornaya Diagnostika 5:6–9 (1994).

Mitragotri et al., "Transdermal Extraction of Analytes Using Low–Frequency Ultrasound", *Pharmaceutical Research*, vol. 17, No. 4 (2000) pp. 466–470.

Mitragotri et al., "Synergistic Effect of Low–Frequency Ultrasound and Sodium Lauryl Sulfate on Transdermal Transport", *Journal of Pharmaceutical Sciences* vol. 89, No. 7 (2000) pp. 892–900.

Mitragotri et al., "Ultrasound–Mediated Transdermal Protein Delivery", *Science*, vol. 269, No. 5225 (1995) pp. 850–853.

Omokhodion et al., "Lead in sweat and its relationship to salivary and urinary levels in normal healthy subjects," *Science Total Environ.* 103:113–122 (1991).

Omokhodion et al., "Sweat lead levels in persons with high blood lead levels: experimental elevation of blood lead by ingestion of lead chloride," *Science Total Environ.* 108:235–242 (1991).

Roizen et al., "A 'Band–Aid' to detect alcohol levels in blood," *Anesthesiology* 73 (3A) :A512 (1990).

Saenger et al., "6–beta hydroxy cortisol, a noninvasive probe to evaluate inhibitory effects of lead on drug metabolism in children," *Pediatr. Res.* 15(4) (Part 2) :501 (Abstr. 367). (Apr. 1981).

Sasaki et al., "Pyrrolidones as penetration enhancers," in Smith et al. (eds.), *Percutaneous Penetration Enhancers*, Chapter 7.1, pp. 211–220, CRC Press (1995).

Stauber et al., "The determination of trace metals in sweat by anodic stripping voltammetry," *Science Total Environ.* 60:263–272 (1987).

Stauber et al., "Percutaneous absorption of inorganic lead compounds," *Science Total Environ.* 145:55–70 (1994).

Swift, "Transdermal measurement of alcohol consumption," *Addiction* 88:1037–1039 (1993).

Taylor et al., "The assessment of biomarkers to detect nephrotoxicity using an integrated database," *Environ. Res.* 75:23–33 (1997).

Walters, "Penetration enhancers and their use in transdermal therapeutic systems," in Hadgraft et al., (eds), *Transdermal Drug Delivery: Development Issues and Research Initiatives*, Chapter 10, pp. 197–246, Marcel Dekker, Inc. (1989).

Wielopolski et al., "Feasibility of noninvasive analysis of lead in the human tibia by soft x–ray fluorescence," *Med. Phys.* 10(2): 248–251 (1983).

Zewert et al., "Creation of transdermal pathways for macromolecule transport by skin electroporation and a low toxicity, pathway–enlarging molecule," *Bioelectrochemistry and Bioenergetics*, vol. 49 (1999) pp. 11–20.

"Monitoring & diagnostics: noninvasive analyzer designed to measure absorbed lead," *Biomedical Technology Information Service* 17(5): 49, 51 (1990).

Shi–Jie et al., "Transdermal absorption of digoxin from plasters and hydrogel patches," *Drug. Des. Delivery* 5:321–28 (1990).

Sugibayashi, et al., "Utility of topical formulations of morphine hydrochloride containing Azone and N–methyl–2–pyrrolidone," *Sel. Cancer Ther.* 5:119–28 (1989).

Akhter et al., "Absorption through human skin of ibuprofen and flurbiprofen; effect of dose variation, deposited drug films, occlusion and the penetration enhancer N–methyl–2–pyrrolidone," *J. Pharm Pharmacol.* 37(1):27–37 (1985).

Bronaugh et al., "Methods for in vitro percutaneous absorption studies IV: The flow–through diffusion cell," *J Pharm Sci.* 74(1):64–7 (Jan. 1985).

Brown et al., "Transdermal Delivery of Drugs," *Ann. Rev. Med.* 39:221–229, 1988.

Brusilow & Gordis, "The permeability of the sweat gland to nonelectrolytes," *Am J Dis Child.* 112(4):328–33 (Oct. 1966).

Burns et al., "Monitoring drug use with a sweat patch: an experiment with cocain," *J Anal Toxicol.* 19(1):41–8 (Feb. 1995).

Danielsson, et al., "Accumulation of toxic metals in male reproduction organs," *Arch Toxicol Suppl.* 7:177–80 (1984).

Glikfeld, et al., "Noninvasive sampling of biological fluids by iontophoresis," *Pharm Res.* 6(11):988–90 (1989).

Hine, et al., "Percutaneous absorption of lead from industrial lubricants," *J Occup Med.* 11(11):568–75 (Nov. 1969).

Lilley, et al., "The use of sweat to monitor lead absorption through the skin," *Sci Total Environ.* 76(2–3):267–78 (1988).

Moore, et al., "The percutaneous absorption of lead–203 in humans from cosmetic preparations containing lead acetate, as assessed by whole–body counting and other techniques," *Food Cosmet Toxicol.* 18(4):399–405 (1980).

Morgan, et al., "Plasma zinc in psoriatic in–patients treated with local zinc applications," *Br J Dermatol.* 102(5):579–83 (1980).

Rao, et al., "Reverse iontophoresis: development of a noninvasive approach for glucose monitoring," *Pharm Res.* 10(12):1751–5 (1993).

Scheuplein et al, "Permeability of the skin," *Physiol Rev.* 51(4):702–47 (Oct. 1971).

* cited by examiner

NON-INVASIVE TRANSDERMAL DETECTION OF ANALYTES

CROSS-REFERENCE TO RELATED APPLICATIONS

This application claims priority to "Non-Invasive Transdermal Detection of Heavy Metals" described in U.S. provisional application serial No. 60/090,459 filed on Jun. 24, 1998, by Larry R. Brown and Elazer R. Edelman.

FIELD OF THE INVENTION

This is generally in the area of non-invasive methods and apparatus for sampling of analytes present in body fluids, including sweat, such as glucose, heavy metals, and compounds of abuse.

BACKGROUND OF THE INVENTION

The development of transdermal methods of delivering drugs through the skin has been made possible by the optimization of solvent conditions of individual drugs so that they solubilize and partition into the stratum corneum skin layer (Brown, L. and Langer, R., "Transdermal Delivery of Drugs," *Ann. Rev. Med.* 39: 221–229, 1988). In addition, transdermal diffusion of drug compounds has been also enhanced using iontophoresis, electroporation and ultrasound. These observations have lead to the further investigation of using the transdermal route to detect metabolites in the skin. Virtually all of the work in the scientific literature has been focused in the area of glucose detection in the treatment of diabetes mellitus. However, large fluctuations in glucose concentrations can occur within minutes after the ingestion of a carbohydrate loaded meal. In contrast, glucose diffusion through the stratum corneum skin layer is relatively slow and lags behind these glycemic variations. Thus, there is a significant "lag time" between the skin measurement of glucose concentration through the stratum corneum skin layer and the actual blood concentration.

Previous attempts restricted to the detection of glucose have not and can not be extended to heavy metals. A more useful and uninvestigated application of transdermal diffusion is to non-invasively detect analytes whose concentration does not vary significantly over short time periods. This is especially important for the detection of chemicals such as heavy metals. For example, a heavy metal such as lithium used to treat manic depressives could be detected by psychiatrists to easily determine patient compliance. The detection of iron would be useful for the detection of iron overload diseases.

Lead (Pb) is an example of a heavy metal which is also a toxic substance. Public health organizations in the United States require all children to be tested several times before beginning school and during their early education. It is required for kindergarten grade entry in many school districts in the United States. Studies indicate that nearly 10% of the children in the United States ages six and under, or 1.7 million children, are victims of lead poisoning (Carolina Environment, Inc. Aug. 8, 1996). The United States Public Health Service estimates one out of six children under the age of six has enough lead in their blood to place them in what scientists consider the risky zone. Childhood lead poisoning has no predilection for socioeconomics or geography.

Although adults are susceptible to lead poisoning, children remain at the highest risk due to the natural instinct to introduce non-food items into their bodies. The effects of lead poisoning include learning disabilities, delinquent behavior, hyperactivity, decreased growth, kidney and heart disease, and even brain damage. Common potential lead-contaminated areas include older play equipment and chipping paint from window and door trim, and even walls.

The symptoms of lead poisoning include headaches, irritability, abdominal pain, vomiting, anemia, weight loss, poor attention span, noticeable learning difficulty, slowed speech development, and hyperactivity. The effects of lead poisoning include reading and learning disabilities, speech and language handicaps, lowered I.Q., neurological deficits, behavior problems, mental retardation, kidney disease, heart disease, stroke, and death.

Current test procedures for lead are traumatic for young children as they require venipuncture and extraction of a blood sample. The scientific literature does not describe non-invasive methodologies for detecting heavy metals via the dermal route.

There are numerous descriptions of the toxicology of Pb absorbed through the skin and then found to result in toxic effects or elevated levels in other tissues. This is especially true in the use of lead for topical cosmetic applications (Moore et al., *Food Cosmet. Toxicol.* 18(4):399–405(1980)) and in industrial applications (Hine et al., *J. Occup. Med.* 11(11):568–75 (1969)). In one citation in the scientific literature, sweat is used to assess the absorption of lead through the skin, but not from systemic blood supply and organs to the skin (Lilley et al., *Science Total Environ.* 76(2–3):267–78 (1988)).

Other examples of plasma heavy metal concentrations caused by skin absorption include zinc (Morgan et al., *Br. J. Dermatol.* 102(5):579–83 (1980)). Cadmium, chromium, and arsenic have also been detected in male reproductive organs (Danielsson et al., *Arch. Toxicol. Suppl.* 7:177–80 (1984)).

Sweat lead detection was well studied by an Australian group at CSIRO, Menai, Australia. Stauber and colleagues worked on sweat lead detection for occupational lead absorption through skin. They found that even inorganic lead can be absorbed through skin and rapidly distributed through the body (Stauber et al., *Science Total Environ.* 145:55–70 (1994)). In one of their experiments (Lilley et al., *Science Total Environ.* 76:267–278 (1988)), lead powder was placed on the left arm of a healthy adult male volunteer, and a certain region of skin of the right arm was induced to sweat for lead detection. The placing of 6 mg of lead as 0.5 M lead nitrate to the left arm resulted in the increase in lead concentration in pilocarpine-induced iontophoresis samples in the right arm. No changes were found in the blood or urine samples. However, Omokhodion and Crockford, *Science Total Environ.* 103:113–122 (1991)) found that there is a good relationship between blood and sweat lead levels among non-occupationally exposed persons.

Many other substances must be measured on a frequent basis, resulting in trauma and pain to the patient. Examples include measuring blood glucose in diabetics and sampling drugs of abuse in cocaine addicts. Efforts for the non-invasive detection of glucose have focused on transdermal extraction of glucose using solvents, iontophoresis or using the penetration of infrared light through the skin. None of these glucose efforts have been commercialized. Among the scientific difficulties associated with glucose detection are that glucose concentrations change transiently and quickly throughout the day, and often do so at rates which exceed the permeability rate of the glucose molecule through the skin.

Therefore the iontophoretic or solvent extraction routes have proven to yield irreproducible data. The use of infrared light has been plagued with interference from other substances of similar structure found in vivo and the inability to calibrate these devices reproducibly.

Transdermal detection of substrates other than lead from sweat has been applied to non-invasive devices. Several transdermal alcohol detection devices have been developed by Dermal Systems International to detect alcohol from sweat (Swift, *Addiction* 88:1037–1039 (1993)). One of those methods is an alcohol dosimeter or "sweat patch" which is a portable, wearable, non-invasive, occlusive patch applied to the skin surface. However, it requires a 7–10 day period for the detection. Another alcohol "Band-Aid®" is a small strip applied to the skin that utilized enzymatic calorimetric detection to estimate blood ethanol concentration over several minutes (Roizman et al., *Anesthesiology* 73(3A):A512, (1990)). However, estimating concentration of a drug (e.g. alcohol) across pharmacokinetic compartments (blood and skin) is not always straightforward. Sweat detection also involves the complexity of both passive diffusion through the skin (Scheuplein and Blank, *Physiological Rev.* 51(4):702–747 (1971)) and active secretion by eccrine glands, primarily sweat glands (Brusilow and Gordis, *Amer. J. Dis. Child* 112:328–333 (1966)).

"Band-Aid®" sweat patches have also been tested in a human clinical study to monitor drug use, for example with cocaine (Burns and Baselt, *J. Analytical Toxicol.* 19:41–48 (1995)). A cellulose based patch collected sweat in a seven day period and substantial cocaine concentrations were detected in the patches. However, quantitative interpretation was beyond the "capabilities of the technology" (Burns and Baselt, supra, at 45, col. 1). This sweat patch was developed by Sudormed, Inc., which was later acquired by Pacific Biometrics, Inc. (Lake Forest, Calif.).

"Reverse" transdermal detection has been used for glucose detection. Because of the non-polar property of the glucose molecule, the "reverse" transdermal glucose detection requires certain enhanced methods, such as iontophoresis and ultrasound. Studies of "reverse" transdermal detection has demonstrated some results for the detection of glucose in the presence of current (Glikfeld et al., *Pharmaceutical Res.* 6(11):988–990 (1989); Rao et al., *Pharmaceutical Res.* 10(12):1751–1755 (1993)). However, all of these methods require complex apparatus to extract the analytes.

It is therefore an object of the present invention to provide a method and apparatus for non-invasively obtaining samples of body fluids for testing for the presence and/or amount of a particular analyte in the body fluid, which is easy and inexpensive.

SUMMARY OF THE INVENTION

A method and apparatus for non-invasive extraction and/or detection of chemicals such as heavy metals and cocaine and analytes such as blood glucose have been developed. A patch or hydrogel containing a reagent such as N-methyl pyrrole, or a similar pyrrolidone or mixture thereof, is used to extract the chemical or analyte to be measured through the epidermis and/or hair. This method is useful for detecting analytes which are generally present in relatively constant blood concentrations. The method is particularly useful for the detection of heavy metals such as lead, lithium, copper, iron, and has been demonstrated to be useful to extract both drugs and metabolic analytes. In the preferred embodiment, the method involves the use of the water miscible solvent N-methyl pyrrolidone (NMP) in an aqueous solution which is incorporated into an adsorbent pad or hydrogel. This adsorbent pad is placed on the skin for a defined time period, removed and then analyzed for the substance of interest. Analytical means can also be incorporated as part of the adsorbent pad in order to conduct both the extraction of the chemical of interest and the assay in situ. Examples demonstrate measurement of lead, cocaine, glucose, and acetaminophen, demonstrating the very broad range of materials which can be extracted. Comparative examples demonstrate that the same results cannot be obtained using other reagents such as dimethylsulfoxide (DMSO).

BRIEF DESCRIPTION OF THE DRAWINGS

FIGS. 7a–7f are graphs of extraction of lead.

DETAILED DESCRIPTION OF THE INVENTION

Compositions and methods for specifically extracting chemicals and chemical compounds, such as heavy metals, through the skin are disclosed. Glucose extraction through the skin with these compositions and methods is also disclosed.

Materials Used for Extraction of Chemical Compounds or Analytes

Extraction Media

The general class of compounds that can be used to extract the compounds to be measured or detected include those pyrrolidones and alkyl pyrrolidones with the following chemical structure which can be co-solubilized with water in order to form a hydrogel using polymers such as poloxamer 407 (Pluronic® F127, or Lutrol® F127, SASF corporation) or polyvinyl alcohol, polyhydroxymethacrylate, or polyhydroxyethylmethacrylate.

Examples of the general chemical structure for the class of compounds used are shown in the figure below. It should be noted that the preferred compounds are 2-pyrrolidone and N-methyl pyrrolidone and most preferred is N-methylpyrrolidone (NMP).

$R_1$=H, $CH_3$, HO—$CH_2$—$CH_2$—, $CH_3$—$CH_2$—, $CH_3$—$(CH_2)_n$ n=1 to 10

$R_3$=H, —OH or an alkyl group such as dodecyl $R_4$ =H, methyloxycarbonyl $R_5$=H, $CH_3$, $CH_3$—$CH_2$—, HO—$CH_2$—$CH_2$.

The following class of pyrrolidones are included: alkyl pyrrolidones and pyrrolidone derivatives; 2-pyrrolidone, 1 methyl-2-pyrrolidone, 1 ethyl 2 pyrrolidone, 1 hexyl-2-pyrrolidone, 1-lauryl-2-pyrrolidone N-(2-hydroxyethyl)-2-pyrrolidone, 1,5-dimethyl-2-pyrrolidone, 5-methyl-2-pyrrolidone, 1-hexyl-4-methyl oxycarbonyl-2-pyrrolidone, 1 lauryl-4-methyl oxycarbonyl-2-pyrrolidone, N-cyclohexyl-2-pyrrolidone, N-dodecyl-2-pyrrolidone, and 1-butyl-3-dodecyl-2-pyrrolidone. For ease of reference, this class of material is generally referred to as NMP. When referenced in the examples, NMP is N-methyl pyrrolidone.

Pharmaceutical grade NMP (Pharmasolve®) is available from International Specialty Products (Wayne, N.J.). Pharmasolve® is presently used as a solvent in a gel in a FDA approved oral dental product developed by Atrix Laboratories (Fort Collins, Colo.). The advantage of NMP is its water miscibility allowing the formation of hydrogels and its excellent safety and toxicity profile.

The examples demonstrate the extraction and solubilization of both water soluble and lipid soluble compounds from the skin. N-methyl pyrrolidone (NMP) and 2-Pyrol® (2-pyrrolidone) (products of GAF) combined with 0.9% NaCl were used to extract and measure the amounts of heavy metals through the skin. Preferably, the NMP and 2-Pyrol® are combined 50/50 with the 0.9% NaCl. The amounts of heavy metals thus extracted are indicative of circulating concentrations of these compounds.

N-methyl-2-pyrrolidone (NMP) has been used as an effective drug delivery skin penetration enhancer. Normal skin is capable of maintaining a reasonably constant level of hydration even when large changes in environment humidity occur. This is because of the presence of a natural moisture factor within the stratum corneum epidermal barrier. The natural moisture factor is believed to consist mainly of free fatty acids, urea, and pyrrolidone carboxylic acid and its sodium salt. Sodium pyrrolidone carboxylate appears to be the principal humectant and increases the water-binding capacity of the stratum corneum. NMP is one of the many analogs of sodium pyrrolidone carboxylate. NMP has shown to increase the transport of steroids, caffeine, ibuprofen, flurbiprofen, and aspirin across skin (Akhter and Barry, *J. Pharm. Pharmacol.* 37:27–37 (1985); Walters, "Penetration Enhancers and their Use in Transdermal Therapeutic Systems," in *Transdermal Drug Delivery: Developmental Issues and Research Initiatives*, Hadgraft et al. (eds.), Marcel Dekker, Inc., 1989). However, NMP has never been used in aqueous admixture to extract any chemical substances from skin.

Carriers

The extraction solvent can be administered as a solution, in an absorbent pad or other material, or in a hydrogel. Diluents are preferably aqueous, most preferably water or 0.9% NaCl. The NMP can also be mixed with, bound to, or incorporated into an absorbant material such as a cellulosic pad, agarose, acrylamide gel or beads, or other materials commonly used as absorbants. Alternatively, the NMP can be incorporated into a hydrogel formed of a preferably hydrophilic polymer or other water miscible materials such as a poloxamer (a polypropylene glycol-polypropyleneoxide block co-polymer) like poloxamer 407 (Pluronic® F127, or Lutrol® F127₁ BASF corporation), polyvinyl alcohol, polyhydroxymethacrylate, polyhydroxyethylmethacrylate, or propylene glycol. Surfactants such as Tween® 20, Tween® 80, Brij® 30 and 36T , menthol, phospholipids, and Azone®.

The pyrrolidone in combination with carrier can be applied directly to the skin and/or hair from which the chemical compound is to be extracted. This will be left in place for a time effective to extract an amount of chemical compound to be detected and/or measured. The mixture may be applied as a device as simple as a Band-Aid® type device, with the pyrrolidone absorbed into the cellulosic pad, or it may be packaged in a small metal or plastic "cup", which is strapped onto the appropriate site using an adhesive, tape, or an outer fabric or leather strap, similar to that worn as part of a watch. The entire device may be disposable or may be refillable.

Compounds to be Detected or Measured

A wide variety of compounds can be extracted using these materials. These include metals such as lead, cadmium, and mercury, organic compounds, especially drugs, such as cocaine, caffeine, and acetaminophen, and biological analytes and/or metabolites, such as glucose.

Lead (Pb) is a particularly important toxic metal to measure and is presently measured in all young children. Other metals which can be extracted include lithium, copper, iron, mercury, and cadmium.

Many drugs are tested, either to establish that a person is adhering to a program to stop a particular addiction (caffeine, cocaine, smoking), or to monitor drug levels (e.g., rheumatoid arthritis patients taking high doses of non-steroidal anti-inflammatories such as acetaminophen). These can all be detected by extracting the chemical compounds into the pyrrolidone containing device.

Other materials to be tested for include metabolic analytes or chemical compounds such as glucose.

The device can include means for detection of these chemical compounds. Detection means may be qualitative or quantitative. Examples include enzyme chromatographic means, such as an enzyme-substrate assay that results in a color change in the presence of substrate; antibody assays, where the antibodies are labeled and migrate to a region where reaction with substrate can be detected. Alternatively, the extracted chemical compound can be removed, for example, using a pipette, capillary tube or syringe type means, and put into a separate detection device such as an HPLC or spectrophotometer.

Kits containing these devices will typically include one or more devices, each of which contains the pyrrolidone/carrier mixture, optionally including devices for removing the extracted chemical compounds from the pyrrolidone/carrier mixture for measurement or detection of the chemical compounds and/or means for measurement or detection of the chemical compounds.

The present invention will be further understood by reference to the following non-limiting examples.

EXAMPLE 1

Extraction of Lead Through Pig Skin in a Diffusion Cell

Figure 1:
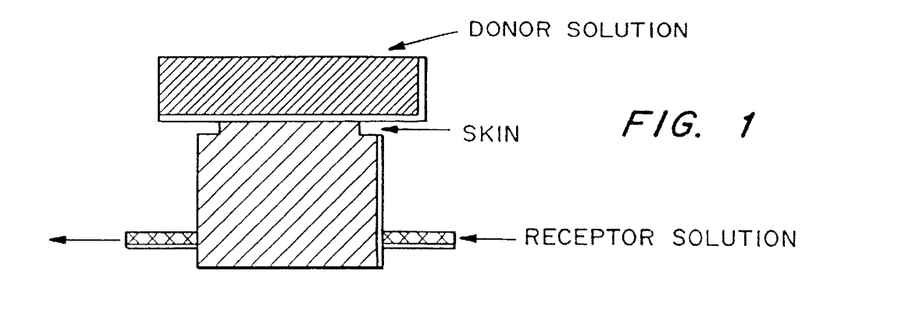
FIG. 1 is a schematic of a flow diffusion cell.

All of the results from the in vitro experiments were conducted using flow Teflon® diffusion cells of the type described by Bronaugh and Steward (*J. Pharm. Sci.* 1985, 74: 64–67). The cross section area of a single diffusion cell was 0.64 cm$^2$. FIG. 1 is a schematic diagram of a typical diffusion cell setup.

Solutions containing 75% N-methyl pyrrolidone (Pharmasolves®, ISP, Wayne, N.J.) (NMP):25% deionized water, 50% NMP:50% deionized water, 25% NMP:75% deionized water and 0% NMP:100% deionized water were used as extraction solvents and placed in the receptor compartment of the diffusion cell shown in FIG. 1. The donor solution contained 5, 10, or 20 µg/ml lead acetate. Samples were measured on an Atomic Absorption Spectrometer (Perkin-Elmer AAnalyst™ 300).

Figure 2:
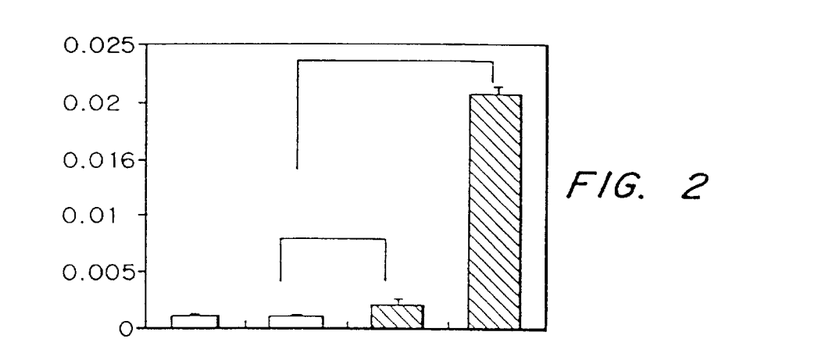
FIG. 2 is a graph of lead extraction through skin at 3 hr (n=3).

Donor solutions containing either 10 µg/ml or 5 µg/ml lead acetate were introduced on the surface of pig skin. The receptor solutions contained either 50% NMP-water or water alone. FIG. 2 shows that there was insignificant diffusion of lead into receptor solutions containing water alone, while those receptor solutions containing 50% NMP:50% water extracted significant amounts of lead at values in excess of 0.02 µg/ml ($p<0.01$, FIG. 2).

EXAMPLE 2

Determination of Optimal NMP Concentration for Lead Extraction

Figure 3:
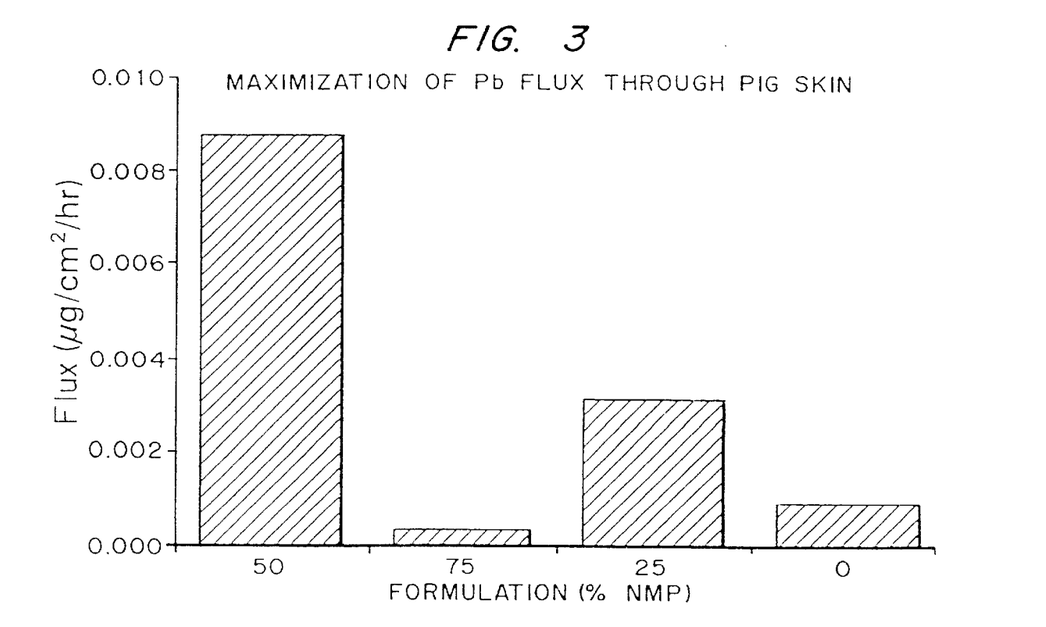
FIG. 3 is a graph of the lead flux ($\mu g/cm^2/hr$) through skin as a function of NMP concentration (0%, 25%, 50%, 75% NMP in water).

In an experiment designed to show that there is an optimal mixture of NMP and water or aqueous buffer, the NMP:deionized H$_2$O solutions were varied between 0 and 75% NMP. Solutions containing 75% N-methyl pyrrolidone (Pharmasolve®, ISP, Wayne, N.J.) (NMP):25% deionized water, 50% NMP:50% deionized water, 25% NMP:75% deionized water and 0% NMP:100% deionized water were used as extraction solvents and placed in the receptor compartment of the diffusion cell shown in FIG. 1. The donor solution contained 20µg/ml lead acetate. The data in FIG. 3 demonstrates the ability of NMP to enhance the extraction of Pb significantly when compared to H$_2$O alone, and that 50% NMP:50% H$_2$O results in the maximum flux when compared to other mixtures of NMP and water.

EXAMPLE 3

Extraction of Lead Over Time Using NMP

Experiments were conducted over a 4 hour period. The donor solutions contained lead acetate at 20 µg/ml, 10 µg/ml, and 5 µg/ml, and 0 µg/ml. The extraction solution contained 50% NMP:50% water.

Figure 4:
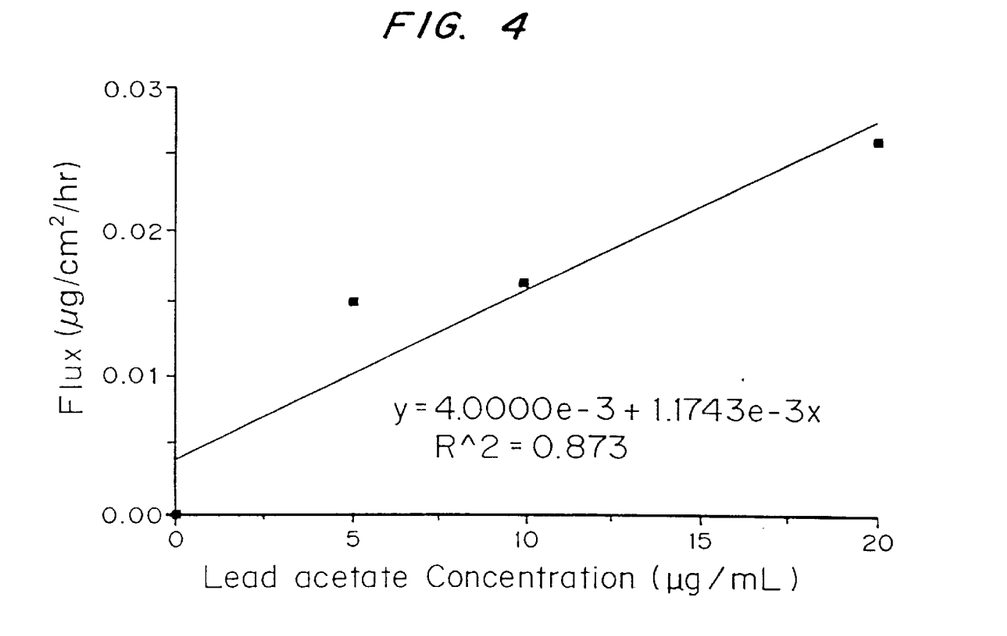
FIG. 4 is a graph of the flux of lead ($\mu g/cm^2/hr$) through swine skin as a function of lead acetate concentration ($\mu g/mL$).

As shown by FIG. 4, the 50% NMP-water solution was capable of extracting lead acetate through the pig skin for up to a 4 hour period, linearly with time and at concentrations as low as 5 µg/ml.

EXAMPLE 4

In vivo Demonstration of the Detectability of Lead Extracted Through the Skin of Rats A clear hydrogel was formed containing 1 gram of the copolymer Pluronic® F127 (BASF) and 2.5 mL of deionized water and 2.5 mL of N-methyl pyrrolidone (Pharmasolve®, ISP, Wayne, N.J.). The hydrogel is easily molded into any shape or container. It also allows and maintains excellent skin surface contact. Lead is introduced into the blood of the rats by feeding the rats with 750 to 1,000 ppm lead acetate drinking water.

Figure 5:
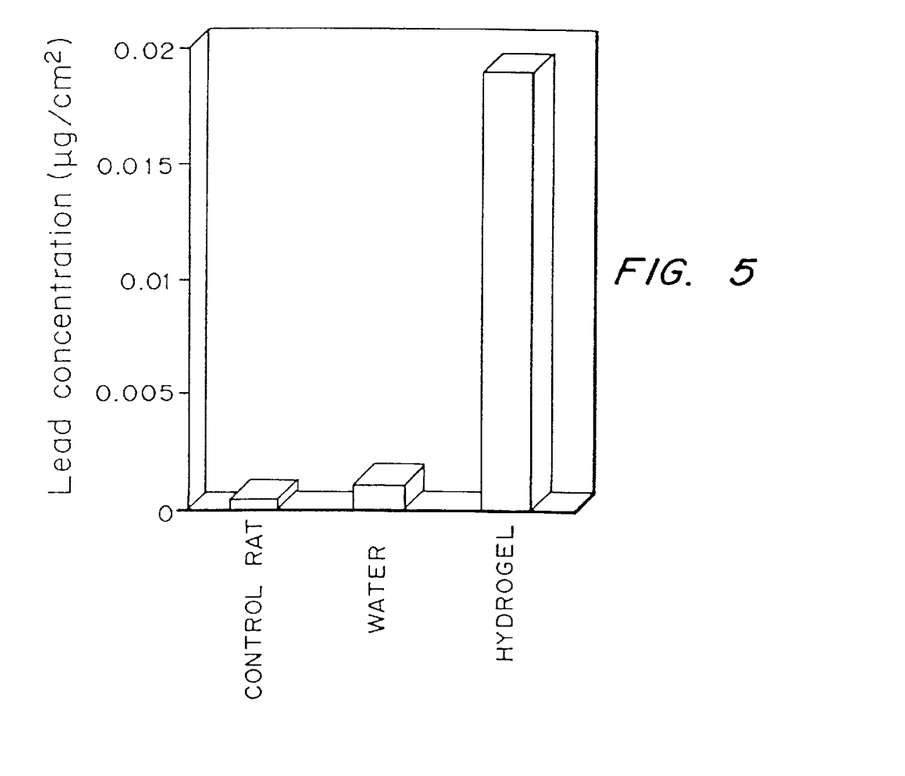
FIG. 5 is a graph of lead concentration ($\mu g/cm^2$) for control rat, water extracted rat, and NMP-hydrogel extracted rat.

FIG. 5 shows that the 50% NMP:50% water Pluronic® hydrogel extracts lead from rats in an in vivo experiment. Each bar represents the mean of 5 rats.

EXAMPLE 5

In vitro Extraction of the Heavy Metals Mercury (Hg) and Cadmium (Cd)

The goal of the in vitro experiments was to prove that NMP could enhance the diffusion of cadmium acetate (Cd) and mercury (Hg) through swine skin. The experiments were conducted in a continuous diffusion cell system. Three diffusion cells contained cadmium acetate (50 µg/ml) in donor chambers and NMP:dH$_2$O (50:50) solution in receptor chambers. Three diffusion cells contained mercury (50 µg/ml) in donor chambers and NMP:dH$_2$O (50:50) solution in receptor chambers. Two diffusion cells contained cadmium acetate (50 µg/ml) in donor chambers and dH$_2$O solution in receptor chambers. Initial samples were taken at 5 min time points. Subsequent samples were taken at 15 min intervals thereafter.

Figure 6:
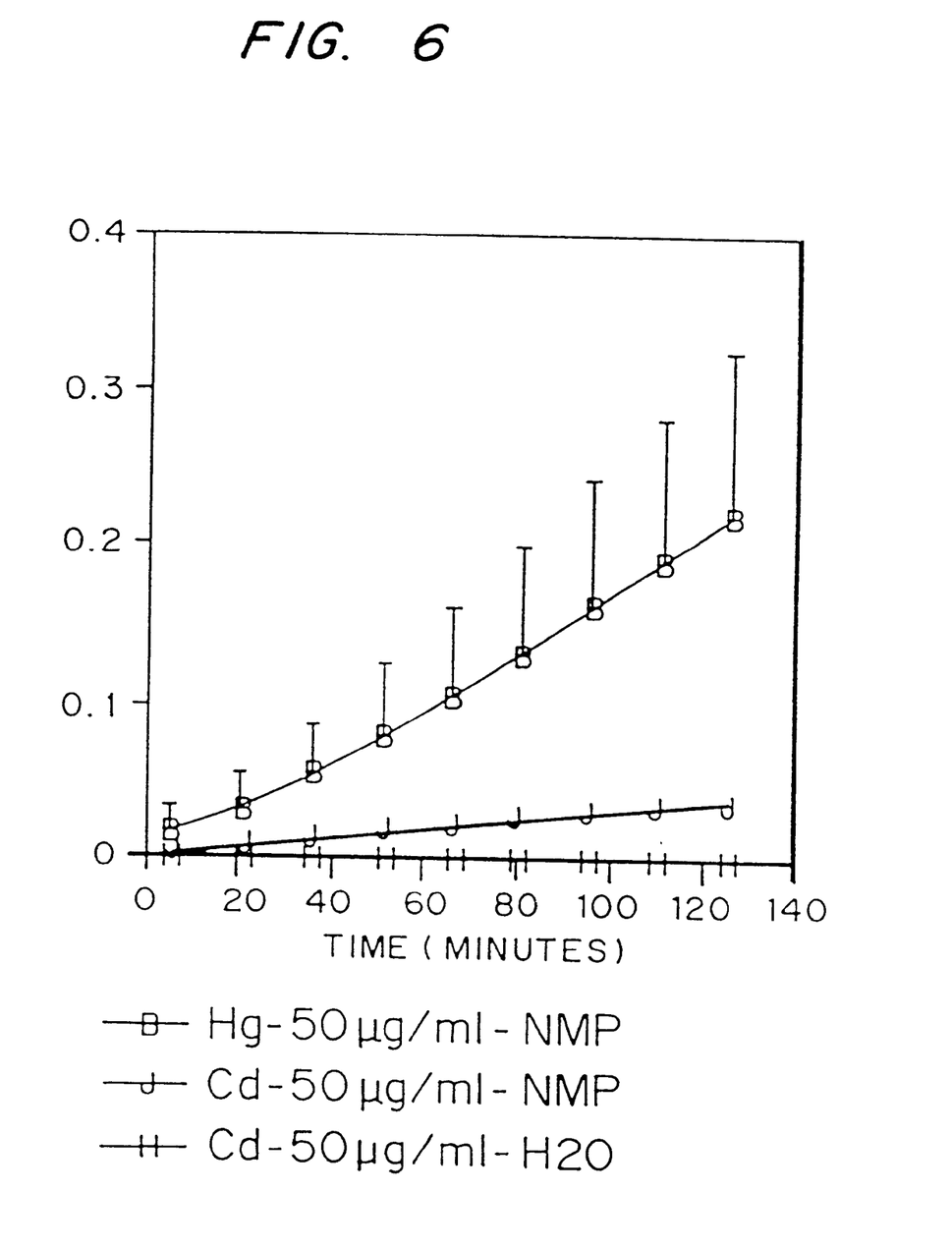
FIG. 6 is a graph of cadmium and mercury extraction through swine skin (n=3) over time (min).

The cadmium acetate concentrations from receptor chambers were measured on graphite Atomic Absorption Spectrometer (Perkin-Elmer AAnalyst™ 300). The mercury concentrations from receptor chambers were measured on flame Atomic Absorption Spectrometer (Perkin-Elmer AAnalyst™ 300). The results are shown in FIG. 6 as X+SD.

The large error bars in Hg extraction was a result of flame AA measurements which generated larger data fluctuations than those of graphite AA measurement which were used for Pb and Cd assays.

The experimental results showed that NMP:dH$_2$O solution enhances the diffusion of cadmium acetate (Cd) through pig skin; NMP:dH$_2$O solution enhances the diffusion of mercury (Hg) through pig skin, and the extraction solvent containing only deionized H$_2$O as a control did not result in significant cadmium extraction from pig skin.

EXAMPLE 6

Figure 7A:
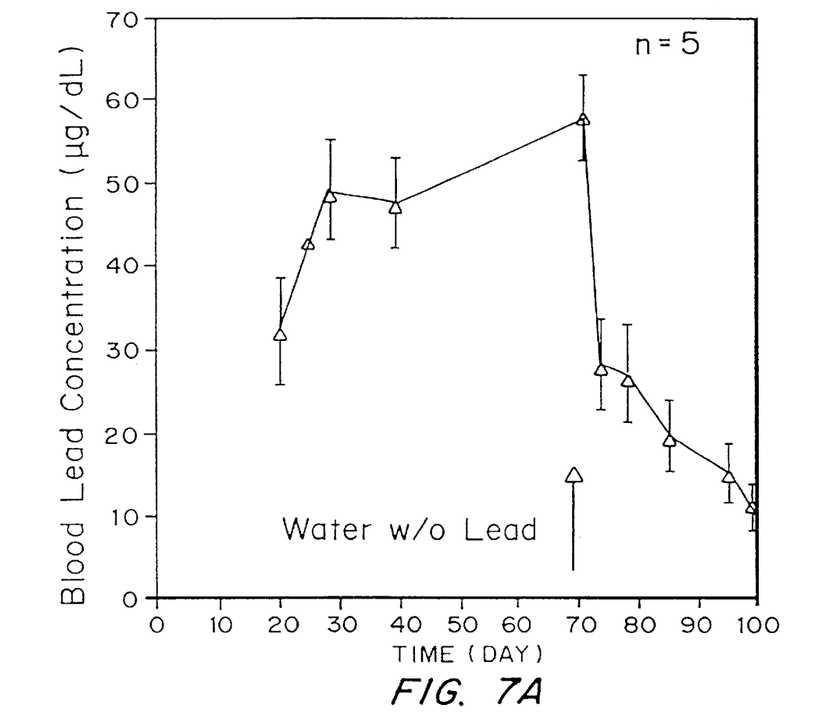
FIG. 7a is a graph of blood lead levels ($\mu g/mL$) in rats over time in days following administration of lead acetate in their drinking water.

In vivo Correlation of Blood Lead and Lead Extracted Through Skin of Rats in vivo Five male Sprague Dawley rats (approximately 400 gms) were fed a diet which contained 750–1,000 ppm lead acetate in their water supply. Determinations of blood lead (Pb) concentrations were conducted by obtaining a blood sample from the tail vein of the animals and analyzing them using an ESA brand LeadCare® Analyzer (Chelmsford, Mass.). After the blood lead levels were determined to be in the 50–60 µg/dL range for several weeks, the leaded drinking water supply was removed (FIG. 7a).

Figure 7B:
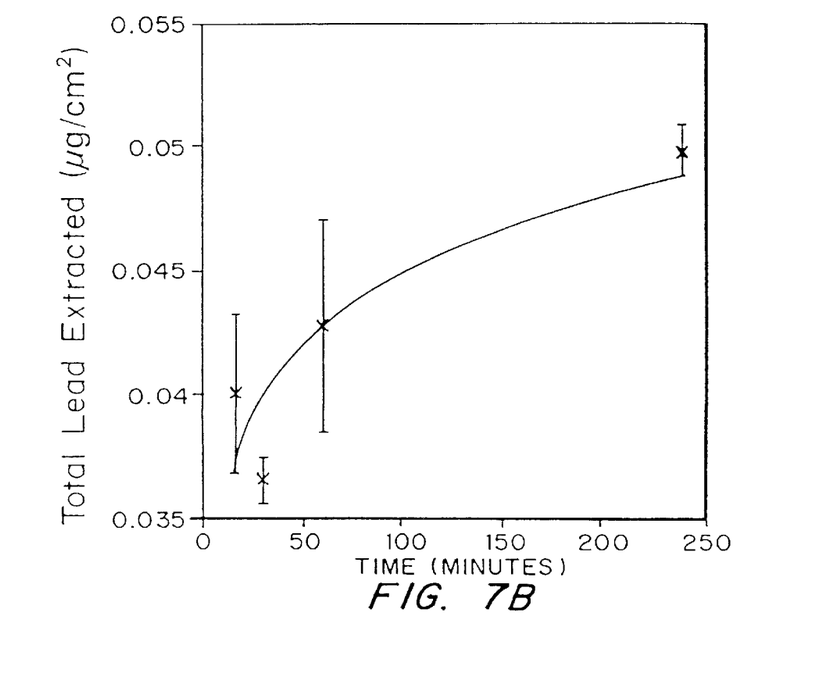
FIG. 7b is a graph of total lead extraction ($\mu g/cm^2$) using NMP-poloxamer over time in minutes.
Figure 7C:
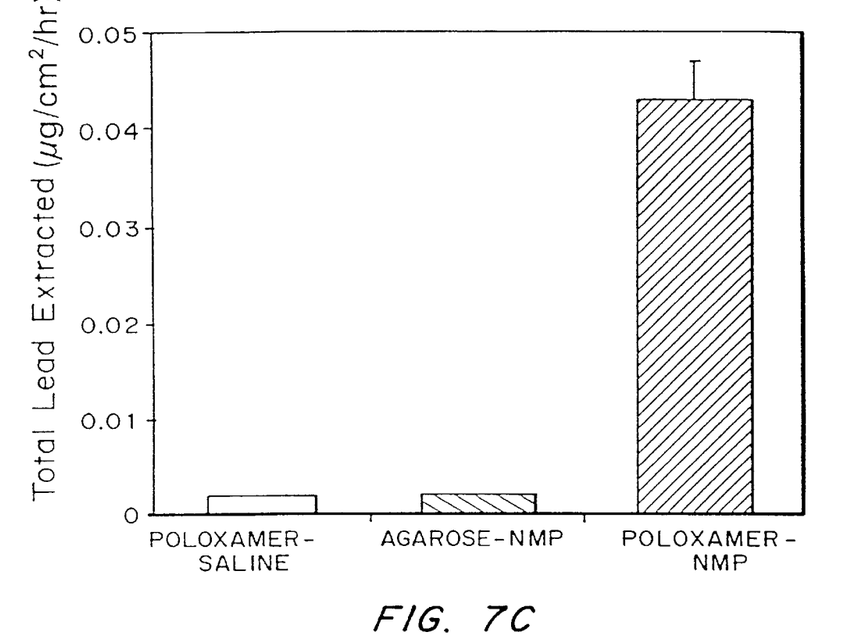
FIG. 7c is a graph of lead extraction with NMP-poloxamer or agarose hydrogel patches.

At that time, a clear hydrogel formulation containing 1 gram of the copolymer Pluronic® F127 (BASP), and 2.0 mL of deionized water and 2.0 mL of N-methyl pyrrolidone (Pharmasolve®, ISP, Wayne, N.J.) was prepared. Approximately 1.2 grams of hydrogel was applied to a 2.4 cm diameter polypropylene plastic disk. The disks were attached to a jacket which was affixed to the backs of the rats. The disks were removed after 1 hour. The NMP-hydrogel was removed and the lead content was determined by atomic absorption spectroscopy (Perkin-Elmer Analyst™ 300). A similar study was conducted using agarose instead of the poloxamer. The data are shown in FIG. 7b as the µg of lead per $cm^2$ over time in minutes and in FIG. 7c as total lead extracted.

Figure 7D:
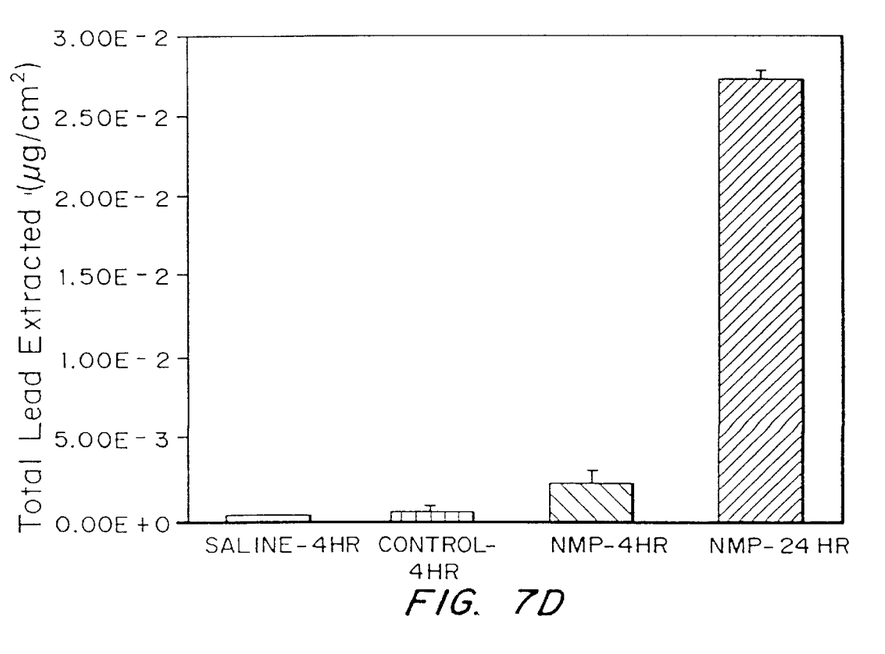
FIG. 7d is a graph of total lead extraction ($\mu g/cm^2$) through rodent skin with NMP-gauze patches, at four and 24 hours.

Similar extractions were made using gauze patches, as shown in FIG. 7d.

Figure 7E:
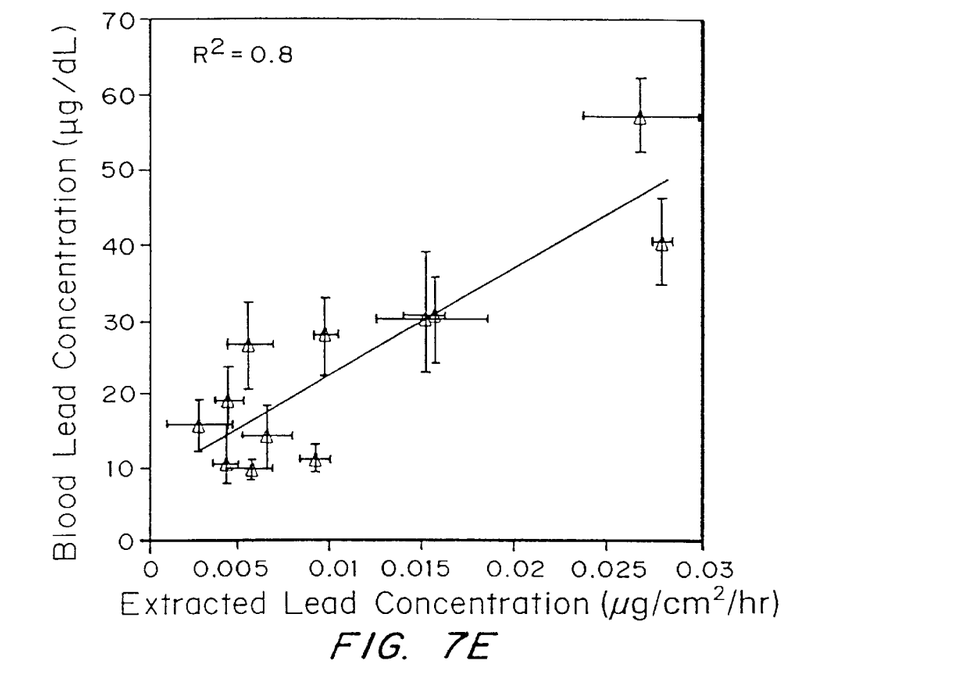
FIG. 7e is a graph of the correlation of the blood lead levels with lead extracted by the NMP-poloxamer hydrogel patches.

FIG. 7e shows the correlation between blood lead concentrations and lead extraction. The data representing 60 blood lead and skin extracted lead determinations clearly demonstrates the NMP-hydrogel's ability to extract significant quantities of lead, which correlate with blood lead concentrations.

Figure 7F:
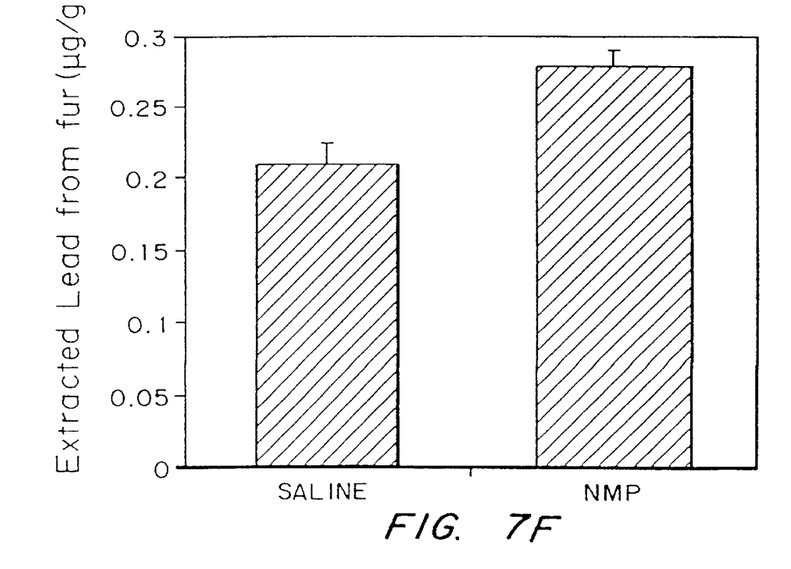
FIG. 7f is a graph showing extraction of lead from rodent fur using NMP-saline.

FIG. 7f demonstrates that lead can also be extracted using the NMP-hydrogel from rodent fur.

EXAMPLE 7

The Detection of Acetaminophen in Human Skin

Two human subjects ingested approximately 5 grams of acetaminophen over a 26 hour period. The acetaminophen was detected through human skin by applying two different hydrogels on the forearm of each subject. One hydrogel contained 25% Lutrol® F127 (Pluronic® F127, BASF) formed with water alone. The second hydrogel was formed by combining 1 gram of the copolymer Pluronic® F127 (Lutrol® P127, BASF) and 2.5 mL of deionized water and 2.5 mL of N-methyl 2-pyrrolidone (Pharmasolve®, ISP, Wayne, N.J.) to form 50% NMP:50% $H_2O$, a clear hydrogel.

Figure 8A:
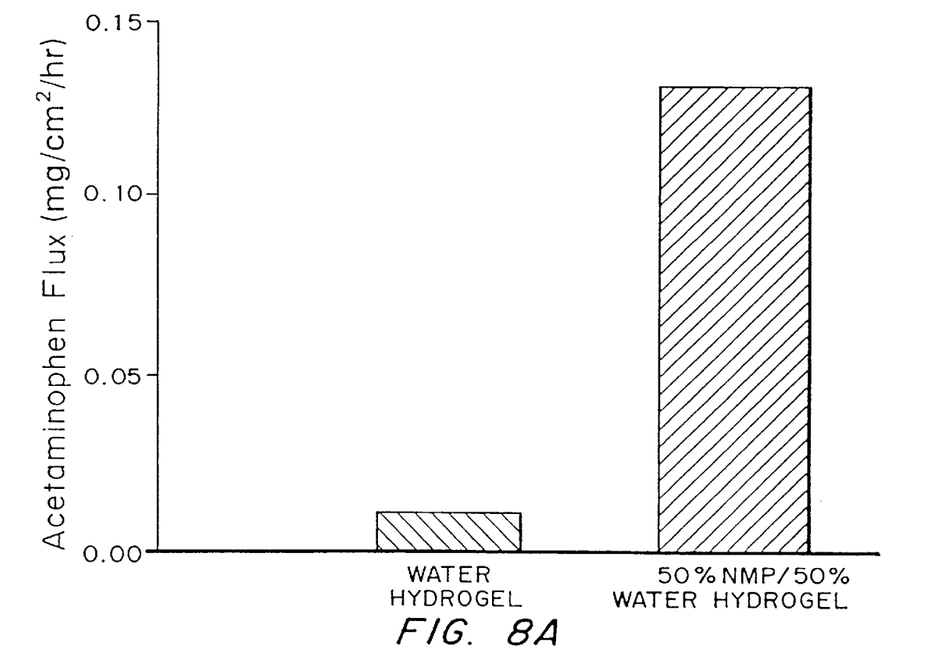
FIG. 8a is a graph of acetaminophen extracted through human skin using 50% NMP:50% water-hydrogel.

The hydrogel is easily molded into any shape or container. It also allows and maintains excellent skin surface contact. Approximately 1.44 gram of the hydrogel was applied to a 10.5 $cm^2$ polypropylene plastic frame. The gel was secured to the test subjects' forearms using surgical tape. The gel was removed after 40 minutes and analyzed using the Sigma Diagnostics acetaminophen assay (catalog #430-A). Samples containing significant concentrations of acetaminophen turn yellow in color. The color intensity was also measured spectrophotometrically. The results are graphed in FIG. 8a, which demonstrates the ability of the NMP:water Pluronic® hydrogel to effectively extract acetaminophen from humans treated with the oral drug by extracting small quantities of acetaminophen through the skin. However, significantly more acetaminophen was extracted when the F127 hydrogel contained 50% NMP:50% water.

A second trial with two subjects yielded total acetaminophen values that were approximately 36% higher for the NMP hydrogel for test subject one and 17% higher for test subject two compared to water only Pluronic® hydrogel.

EXAMPLE 8

Extraction of Acetaminophen in Human Skin Using Alternate Hydrogels

Using the techniques in Example 7, 50% NMP:50% water was loaded into Pluronic® 127, polyvinyl alcohol, Sephadex® and agarose. The gels were placed on a test subjected who had ingested 1 gram of acetaminophen for 45 minutes. The gels were analyzed for acetaminophen using the Sigma Diagnostics acetaminophen assay (catalog #430-A).

Yellow color development was greatest with the Pluronic® F127 formulation. The polyvinyl alcohol formulation also showed the extraction of acetaminophen, however the yellow color development was less than the Pluronic® F127 formulation. Little or no yellow color change was seen with the agarose or Sephadex® gels.

EXAMPLE 9

Extraction of Acetaminophen in Human Skin Using Alternate Pyrrolidone Derivatives 4 grams of acetaminophen was orally ingested at a dose equal to 1000 mg every 6 hours over a 26 hour period by a human subject.

1 gram Pluronic® F-127 was dissolved in either:

4 mL of water (water hydrogel), or 4 mL of a 50% by volume solution of N-methyl-2-pyrrolidone-water (NMP-hydrogel), or 4 mL of a 50% by volume solution of 2-pyrrolidone-water (2-pyrrolidone hydrogel).

Approximately 1.25 gram of the hydrogel was applied to a 10.5 $cm^2$ polypropylene plastic disk. The plastic disk containing the hydrogel was secured to the test subject's forearm using surgical tape. The gel was removed after 40 minutes and analyzed using the Sigma Diagnostics acetaminophen assay (catalog # 430-A). Samples containing significant concentrations of acetaminophen turn yellow in color. The color intensity was also measured spectrophotometrically.

Figure 8B:
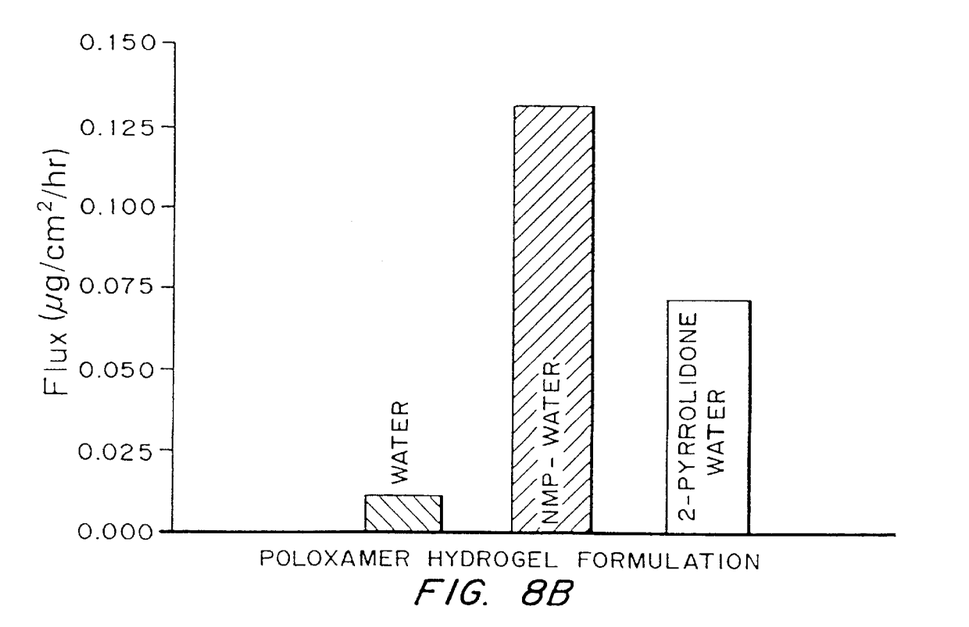
FIG. 8b is a graph comparing extraction of acetaminophen through human skin with NMP-water versus 2-pyrrolidone-water.
Figure 9:
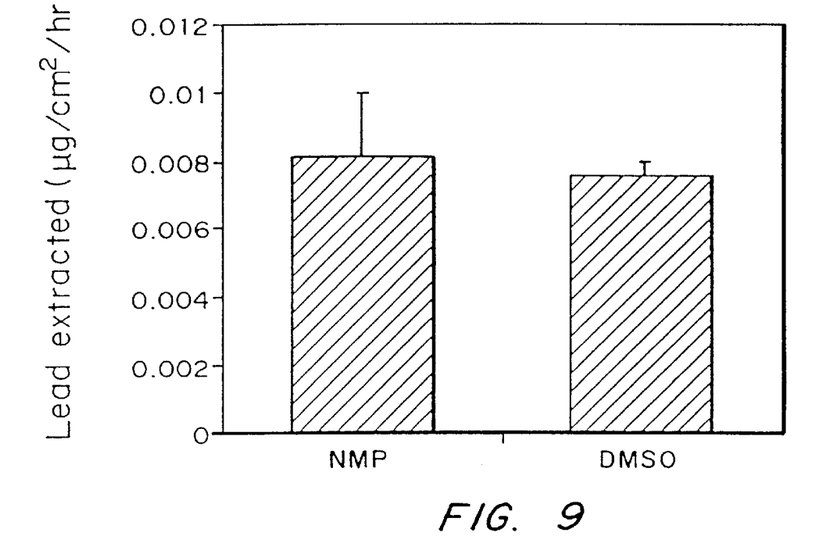
FIG. 9 is a graph comparing extraction of lead ($\mu g/cm^2/hr$) through rat skin using either 50% NMP:50% water hydrogel or 25% DMSO-hydrogel.

The results are shown in FIG. 8b. Yellow color development was greatest with the NMP-hydrogel. A significant amount of acetaminophen was also recovered using the 2-pyrrolidone hydrogel. Only very small quantities of acetaminophen was detected using the water only hydrogel. Thus, it appears that the transdermal extraction of acetaminophen can be accomplished with the general class of alkyl (N-methyl) and H (2-pyrrolidone) substituted pyrrolidone transdermal enhancing agents.

EXAMPLE 10

The Detection of [$^{14}C$]-caffeine Administered to Rats Through Skin

Rats were shaven and fasted for 24 hours prior to caffeine administration by intraperitoneal injection of $^{14}C$ labeled caffeine to the 600 gram rats. Each animal received approximately 16.7 µCi of $^{14}C$ caffeine via intraperitoneal injection of 0.5 mL of ethanol and water.

A 50% NMP:50% water-Pluronic® F127 hydrogel was applied to 2.4 cm diameter plastic disks. The disks were attached to a jacket which was affixed to the backs of the rats. The disks were removed after 2.5 hours. The gel was removed and counted. The rats were sacrificed and blood and tissue were removed for analysis from each animal. The tissue samples were placed in liquid scintillation vials with 1.5 mL of Soluene® (Packard Instruments, Downers Grove, Ill.) in order to dissolve the tissues for valid liquid scintillation counting.

The table below shows the relative amounts of radioactivity found in each of the samples.

| Sample | Radioactivity (mean dpm ± SD) |
|---|---|
| Skin | 52.15 ± 0.07 dpm/mg |
| Muscle | 64.30 ± 8.73 dpm/mg |
| Blood | 87.24 dpm/μL |
| NMP-Pluronic ® F127 Hydrogel | 58.82 dpm/cm$^2$/hr |

The data demonstrate that the tissue, skin and blood concentration of $^{14}$C labeled caffeine are of the same order of magnitude. This suggests that the ability to extract drugs from the skin should result in a value which is representative of the animal's steady state concentrations of the drug, molecule or chemical. Indeed, the data in the table show that the NMP containing hydrogel was shown to extract a significant quantity of radioactive caffeine through the rat.

EXAMPLE 11

In vitro Extraction of Cocaine $^3$H-cocaine transport through swine skin was conducted with diffusion cells (4.5 cm diameter). $^3$H-cocaine donor solution (20 μCi/ml) was loaded in the upper chamber. The receptor solution (50% NMP:H$_2$O) was loaded in the lower chamber. Samples from the lower chamber (100 μl) were taken every hour and counted.

Figure 10:
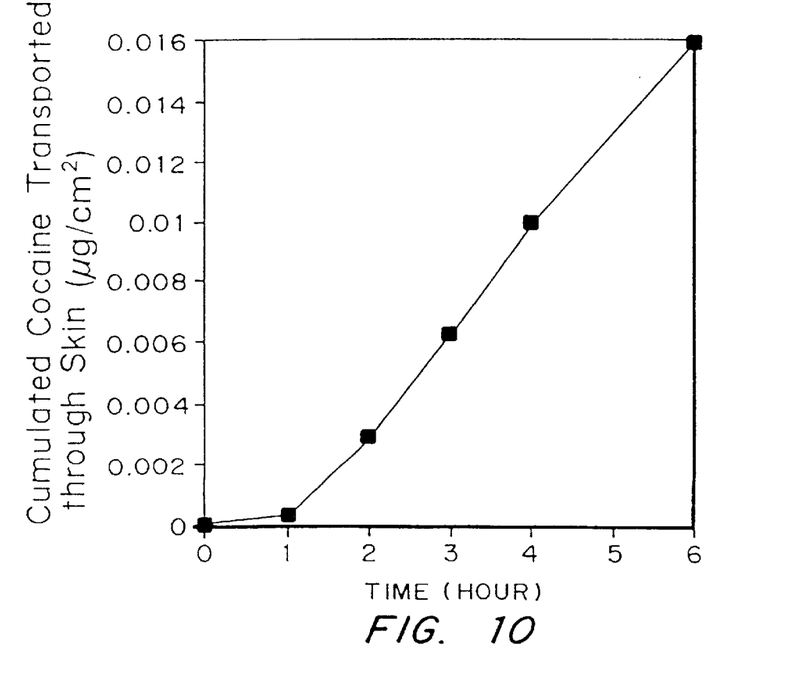
FIG. 10 is a graph of cumulated cocaine transported through skin ($\mu g/cm^2$) over time in hours.

The results are shown in FIG. 10. The flux of $^3$H-cocaine through pig skin in vitro was determined to be 0.00317 μg/cm$^2$/hr.

EXAMPLE 12

In vivo Extraction of Cocaine

Rats (500–600 g) were shaven prior to cocaine administration by intraperitoneal injection of $^3$H-cocaine (20 μCi/ml). Each animal received a dose of approximately 40 μCi. Using the techniques described in Example 8, both NMP-:poloxamer and water:poloxamer patches were applied to the shaved rat skin. The hydrogel patches were removed after two hours. The hydrogel was collected and the amount of $^3$H-cocaine extracted in hydrogel was counted by liquid scintillation counting.

Figure 11:
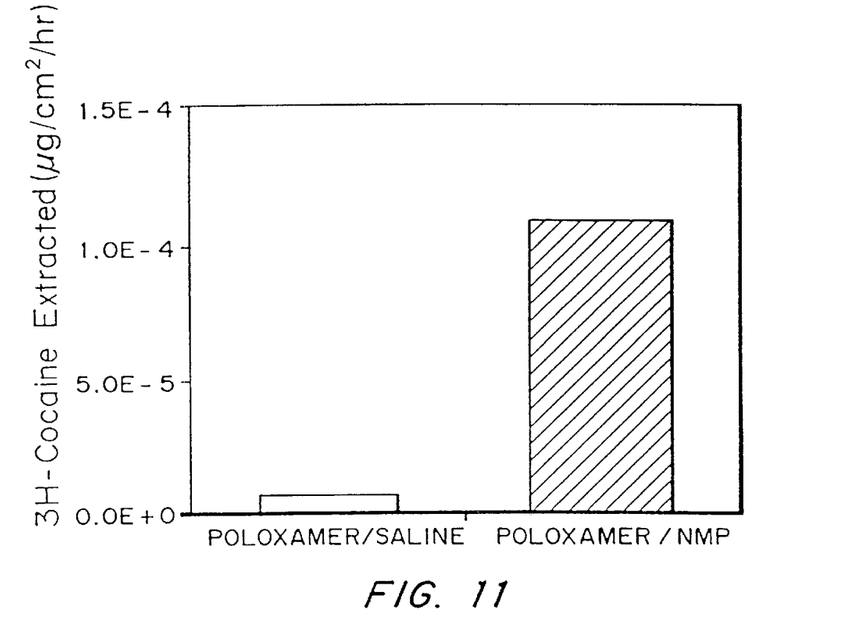
FIG. 11 is a graph of cocaine extracted ($\mu g/cm^2/hr$) by either poloxamer or NMP-poloxamer.

The results are shown in FIG. 11.

EXAMPLE 13

Comparison of Extraction Using Either NMP or DMSO from Swine Skin (in vitro) or Rats (in vivo)

In vitro extraction of lead acetate by NMP and DMSO through swine skin was conducted with diffusion cells (4.5 cm diameter). Lead acetate donor solution (200 μg/ml) was loaded in upper chamber. The receptor solution (50% NMP:H$_2$O) was loaded in lower chamber. Samples from lower chamber (1 ml) were taken every hour and measured by atomic absorption spectroscopy.

Figure 12:
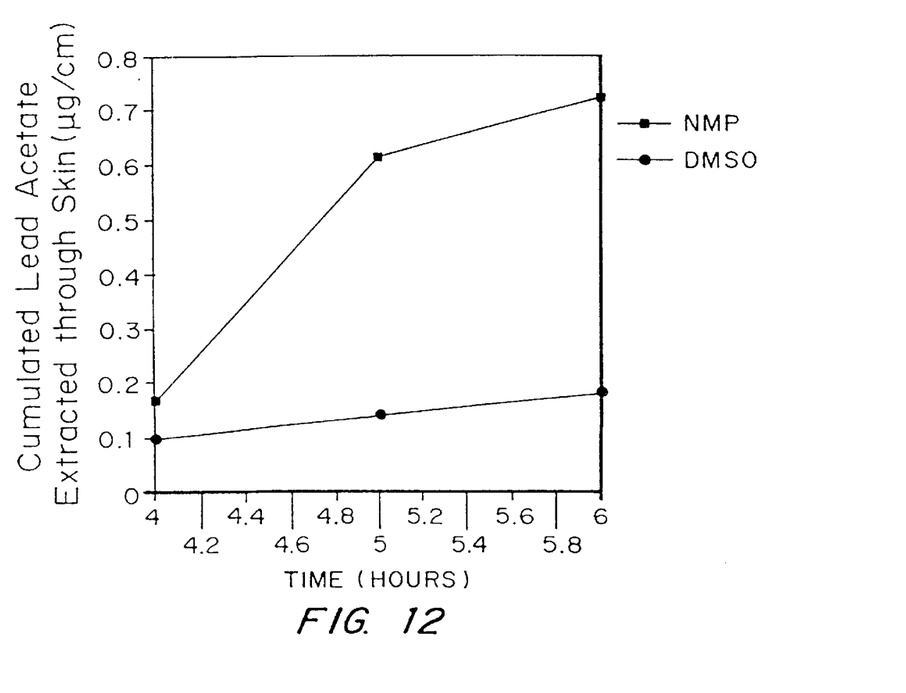
FIG. 12 is a graph of cumulated lead acetate extracted through swine skin over time, comparing 50% DMSO (circles) and 50% NMP (squares).

The results are shown in FIG. 12. The fluxes for lead acetate through swine skin for NMP and DMSO as extraction agents are 0.279 μg/cm$^2$/hr and 0.040 μg/cm$^2$/hr respectively.

Rats fed with lead acetate were used in the experiment. Poloxamer hydrogel patches contained 50% NMP or 25% DMSO were applied to the shaved rat skin. The hydrogel patches were removed after one hour. Hydrogel was collected and the amount of lead extracted in hydrogel was measured on AA.

Figure 13:
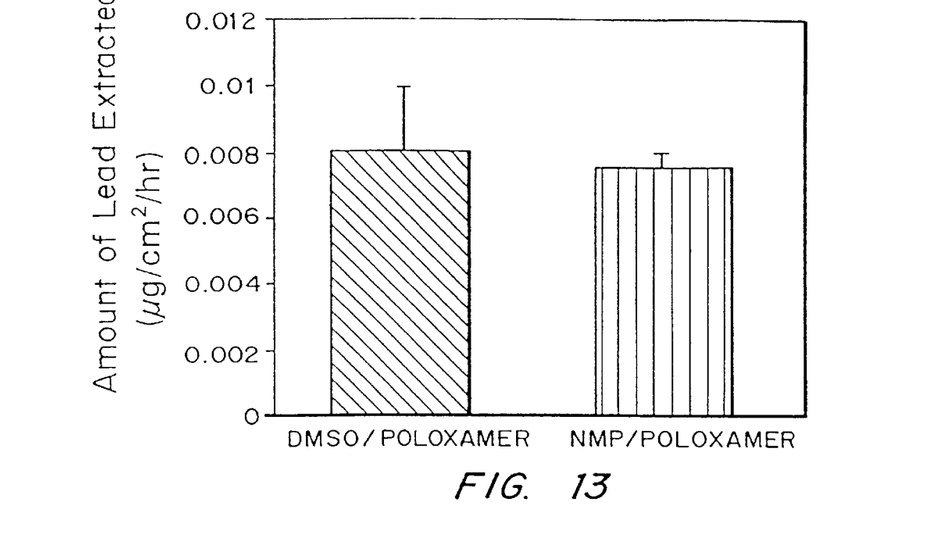
FIG. 13 is a graph of the amount of lead extracted through rat skin ($\mu g/cm^2/hr$) comparing 50% NMP-poloxamer with 25% DMSO-poloxamer.

The results are shown in FIG. 13.

EXAMPLE 14

Extraction of Glucose from Human Skin Using NMP or 2-Pyrol® Aqueous Solutions

N-methyl-2-pyrrolidone (NMP) and 2-Pyrol® (2-pyrrolidone) combined in 50% by volume and 50% by 0.9% NaCl in aqueous solution have been shown to allow significant glucose concentrations measurement through the skin.

NMP or 2-Pyrol® were mixed in equal volumetric proportions with 0.9% NaCl solution in water. In addition, a solution containing 0.9% NaCl alone was prepared. The skin on the forearm was thoroughly washed with soap and water and swabbed clean with 70% isopropyl alcohol. Approximately 25 μl of a 50:50 solution of NMP:0.9% NaCl solution in H$_2$O or the 0.9% NaCl solution were placed on the forearm for a 5–10 minute period contained within a foil backed adhesive with a circular opening in the center. At the end of the sampling period, an additional 10 μl was then placed on the skin and used to recover the test solutions. An approximate 5 to 10 μl drop was applied to a MediSense® ExacTech® (Abbott Laboratories) glucose test strip. The normal glucose determination procedure described in the ExacTech® brochure was followed for the determination of glucose concentration using the ExacTech® meter.

Simultaneously, capillary blood samples were obtained from a diabetic subject and glucose concentrations were measured with the Medisense Exactech meter as described in their device brochure. A small drop of blood was obtained and placed on the ExacTech® strip and measured for glucose concentration.

The results are tabulated below.

| Measurements of Glucose in Blood Compared to Skin Extraction | | |
|---|---|---|
| Blood glucose (mg/dl) | Skin Glucose (mg/dl) | 0.9% NaCl in H$_2$O |
| 159 | 42 (5 min skin application of test solution) 54 (10 min skin application of test solution) | LO (below detection) |
| 207 | 66 49 | LO |

The results demonstrate that the NMP:0.9% NaCl solution was effective in enhancing the ability to detect glucose on the skin compared to the 0.9% NaCl control, and that the formulation appears to enable one to detect skin glucose. However, the skin glucose values measured were approximately ⅓ those of the blood glucose values. The NaCl in the water control indicates the importance of the penetration enhancing qualities offered by the NMP used to "extract" the glucose from the skin.

EXAMPLE 15

Effect of Time on Glucose Concentration Collection from Skin

NMP or 2-Pyrol® (2-pyrrolidone) were mixed in equal volumetric proportions with 0.9% NaCl solution in water. In addition, a solution containing 0.9% NaCl alone was prepared. The skin on the forearm was thoroughly washed with soap and water and swabbed clean with 70% isopropyl alcohol. Approximately 25 µl of the 50:50 solution of NMP:0.9% NaCl solution in H$_2$O or the 0.9% NaCl solution was placed on the forearm and samples were measured over a 75 minute period from within a foil backed adhesive with a circular opening in the center to contain the test solution. An approximate 5 to 10 µl drop was applied to a MediSense® ExacTech® glucose test strip. The normal glucose determination procedure described in the ExacTech® brochure was followed for the determination of glucose concentration using the ExacTech® meter.

Figure 14:
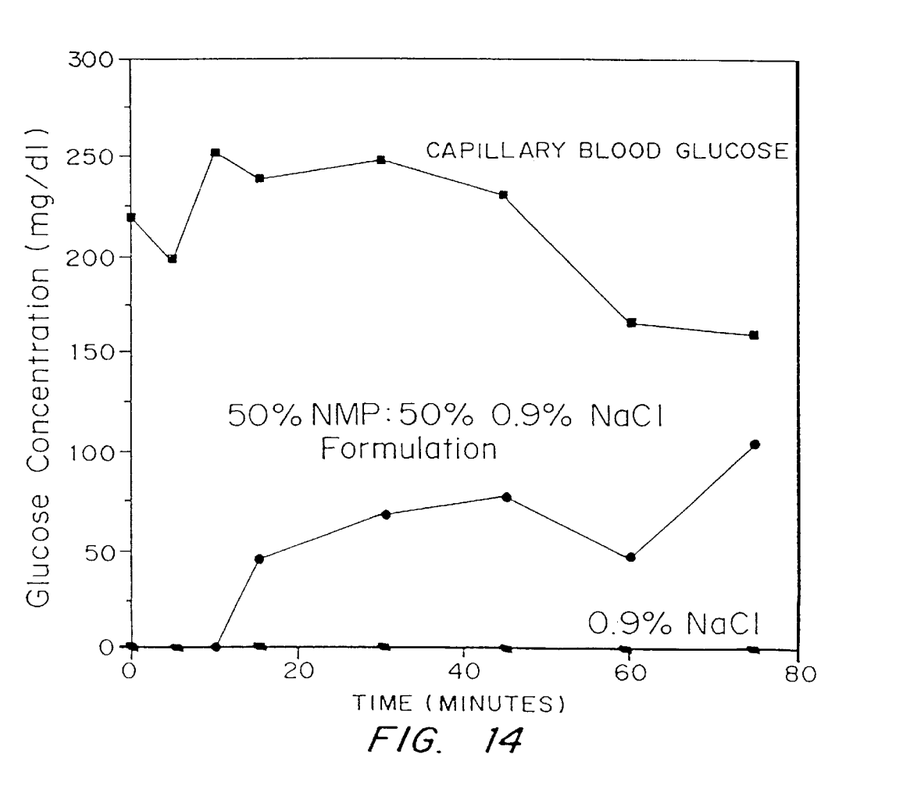
FIG. 14 is a graph comparing glucose concentration extracted using 50% NMP:50% NaCl (0.9%) with capillary blood glucose (mg/dl) over time (min).

Simultaneously, capillary blood samples were obtained from a diabetic subject and glucose concentrations were measured with the MediSense® ExacTech® meter as described in their device brochure. A small drop of blood was obtained and placed on the ExacTech® strip and measured for glucose concentration. The results of the time course experiment are shown in FIG. 14.

The data indicate that glucose extraction from the skin is not measurable using the 0.9% NaCl test solution. In contrast, and after a 15 minute lag time, the sampling of the 50% NMP:50% 0.9% NaCl solution resulted in significant and measurable skin glucose concentrations over the course of the experiment.

We claim:

1. A method for the noninvasive transdermal detection of analytes present within a mammalian subject, comprising:
   contacting the skin of said subject with a pyrrolidone of the following formula in aqueous admixture, wherein
   $R_1$=H, CH$_3$—, HO—CH$_2$—CH$_2$—, CH$_3$—CH$_2$—, or CH$_3$—(CH$_2$)$_n$—, wherein n=1 to 11,
   $R_3$=H, —OH, CH$_3$—, or CH$_3$—(CH$_2$)$_n$—, wherein n=1 to 11,
   $R_4$=H, or methyloxycarbonyl, and
   $R_5$=H, CH$_3$—, CH$_3$—CH$_2$—, or HO—CH$_2$—CH$_2$,
   for a time, no longer than 2 hours, sufficient to permit detectable amounts of said analyte to be extracted from said subject into said aqueous pyrrolidone mixture; and then
   detecting said extracted analyte,
   wherein said analyte is a heavy metal.

2. The method of claim 1, wherein said pyrrolidone is selected from the group consisting of N-methyl 2-pyrrolidone, 2-pyrrolidone, 1-methyl-2-pyrrolidone, 1-ethyl-2-pyrrolidone, 1-hexyl-2-pyrrolidone, 1-lauryl-2-pyrrolidone, N-(2-hydroxyethyl)-2-pyrrolidone, 1,5-dimethyl-2-pyrrolidone, 5-methyl-2-pyrrolidone, 1-hexyl-4-methyloxycarbonyl-2-pyrrolidone, 1-lauryl-4-methyloxycarbonyl-2-pyrrolidone, N-cyclohexyl-2-pyrrolidone, N-dodecyl-2-pyrrolidone, and 1-butyl-3-dodecyl-2-pyrrolidone.

3. The method of claim 2, wherein said pyrrolidone is N-methyl 2-pyrrolidone (NMP) or 2-pyrrolidone.

4. The method of claim 3, wherein said pyrrolidone is N-methyl 2-pyrrolidone (NMP).

5. The method of claim 1, wherein said pyrrolidone is admixed with water.

6. The method of claim 1, wherein said pyrrolidone is admixed with saline.

7. The method of claim 1, wherein said pyrrolidone is at an aqueous concentration of 25% (v/v).

8. The method of claim 1, wherein said pyrrolidone is at an aqueous concentration of 75% (v/v).

9. The method of claim 7 or claim 8, wherein said pyrrolidone is NMP.

10. The method of claim 4, wherein said NMP is present at an aqueous concentration of 50% (v/v).

11. The method of claim 1, wherein said aqueous pyrrolidone mixture is included within a hydrogel.

12. The method of claim 1, wherein said aqueous pyrrolidone mixture is included within an absorbant.

13. The method of claim 12, wherein said absorbant is selected from the group consisting of cellulosic pad and gauze patch.

14. The method of claim 1, wherein said time is no more than 75 minutes.

15. The method of claim 1, wherein said time is no more than 60 minutes.

16. The method of claim 1, wherein said analyte detected within said aqueous pyrrolidone mixture.

17. The method of claim 1, further comprising the step, prior to detecting said analyte, of:
   separating said extracted analyte from said pyrrolidone mixture.

18. The method of claim 1, wherein said analyte detection is qualitative.

19. The method of claim 1, wherein said analyte detection is quantitative.

20. The method of claim 1, wherein said analyte is detected colorimetrically.

21. The method of claim 1, wherein said analyte is detected spectrophotometrically.

22. The method of claim 1, wherein said analyte is detected chromatographically.

23. The method of claim 1, wherein said analyte is detected by immunoassay.

24. The method of claim 1, wherein said heavy metal is selected from the group consisting of lead, cadmium, mercury, lithium and copper.

25. The method of claim 24, wherein said heavy metal is lead.

26. The method of claim 24, wherein said heavy metal is cadmium.

27. The method of claim 24, wherein said heavy metal is mercury.

28. The method of claim 24, wherein said heavy metal is lithium.

29. The method of claim 24, wherein said heavy metal is copper.

* * * * *